(12) United States Patent
Subramanian et al.

(10) Patent No.: US 10,414,700 B2
(45) Date of Patent: Sep. 17, 2019

(54) PROCESS FOR PRODUCING CUMENE AND/OR SEC-BUTYLBENZENE USING A MIXED OLEFINS STREAM AS ALKYLATION AGENT

(71) Applicant: SABIC GLOBAL TECHNOLOGIES B.V., Bergen op Zoom (NL)

(72) Inventors: Selvakumar Subramanian, Karnataka (IN); Dimitri Daniëls, Geleen (NL); Kae Shin Wong, Geleen (NL); Andrew Mark Ward, Stockton-on-Tees (GB)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 15 days.

(21) Appl. No.: 15/758,062

(22) PCT Filed: Sep. 1, 2016

(86) PCT No.: PCT/EP2016/070648
§ 371 (c)(1),
(2) Date: Mar. 7, 2018

(87) PCT Pub. No.: WO2017/042088
PCT Pub. Date: Mar. 16, 2017

(65) Prior Publication Data
US 2018/0179123 A1 Jun. 28, 2018

(30) Foreign Application Priority Data
Sep. 7, 2015 (EP) .................................... 15184105

(51) Int. Cl.
| | | |
|---|---|---|
| *C07C 2/66* | (2006.01) | |
| *C07C 37/58* | (2006.01) | |
| *C07C 45/36* | (2006.01) | |
| *C07C 2/00* | (2006.01) | |
| *C07C 1/20* | (2006.01) | |
| *C07C 407/00* | (2006.01) | |
| *B01J 29/08* | (2006.01) | |
| *B01J 29/18* | (2006.01) | |
| *B01J 29/70* | (2006.01) | |

(52) U.S. Cl.
CPC .................. *C07C 2/66* (2013.01); *C07C 1/20* (2013.01); *C07C 2/00* (2013.01); *C07C 37/58* (2013.01); *C07C 45/36* (2013.01); *C07C 407/00* (2013.01); *B01J 29/084* (2013.01); *B01J 29/18* (2013.01); *B01J 29/7007* (2013.01); *C07C 2529/08* (2013.01); *C07C 2529/70* (2013.01); *Y02P 20/52* (2015.11)

(58) Field of Classification Search
CPC ....... C07C 2/66; C07C 15/02; C07C 2529/70; C07C 45/36; C07C 37/58; C07C 15/073; C07C 15/085; C07C 39/04; C07C 49/08; C07C 49/10; C07C 1/20; C07C 2529/08; C07C 2/00; C07C 407/00; B01J 29/084; B01J 29/18; B01J 29/7007
See application file for complete search history.

(56) References Cited

U.S. PATENT DOCUMENTS

| | | |
|---|---|---|
| 3,763,259 A | 10/1973 | Hervert |
| 4,262,151 A | 4/1981 | Pujado |
| 4,387,259 A | 6/1983 | Barile |
| 4,450,303 A | 5/1984 | Drake |
| 5,902,917 A | 5/1999 | Collins et al. |
| 6,002,057 A * | 12/1999 | Hendriksen ............... C07C 2/66 |
| | | 203/DIG. 6 |
| 6,630,608 B2 | 10/2003 | Tanger et al. |
| 7,759,524 B2 | 7/2010 | Buchanan et al. |
| 7,799,956 B2 | 9/2010 | Cheng et al. |
| 7,812,196 B2 | 10/2010 | Dakka et al. |
| 7,939,693 B2* | 5/2011 | Cheng ....................... C07C 2/66 |
| | | 568/385 |
| 8,436,213 B2 | 5/2013 | Dakka et al. |
| 2006/0178544 A1 | 8/2006 | Murray et al. |
| 2008/0033217 A1 | 2/2008 | Dakka et al. |
| 2008/0194896 A1 | 8/2008 | Brown et al. |
| 2009/0112029 A1 | 4/2009 | Schultz |
| 2009/0312580 A1 | 12/2009 | Cheng et al. |

FOREIGN PATENT DOCUMENTS

| | | |
|---|---|---|
| CN | 102050693 A | 5/2011 |
| WO | 2004074230 A1 | 9/2004 |
| WO | 2015112293 A1 | 7/2015 |

OTHER PUBLICATIONS

Baerlocher et al., "Atlas of Zeolite Framework Types", Fifth Revised Edition, 2001, 17 pages.
Czaplewski et al., "One-dimensional zeolites as hydrocarbon traps", Microporous and Mesoporous Materials 56, 2002, pp. 55-64.
European Search Report for European Application No. 15184105.3, dated Feb. 15, 2016, 4 pages.
Hwang and Chen, "Cumene", Kirk-Othmer Encyclopedia of Chemical Technology, 2010, pp. 1-10.
Hwang and Chen, "Phenol", Kirk-Othmer Encyclopedia of Chemical Technology, 2010, pp. 1-11.
International Search Report for International Application No. PCT/EP2016/070648, International Filing Date Sep. 1, 2016, dated Apr. 11, 2016, 3 pages
Konno et al., "Effectiveness of nano-scale ZSM-5 zeolite and its deactivation mechanism on catalytic cracking of representative hydrocarbons of naphtha", Microporous and Mesoporous Materials 175, 2013, pp. 25-33.
Laredo et al., "Benzene reduction in gasoline by olefin alkylation: Effect of the catalyst on a C6-reformate heart-cut", Catalysis A: General, 2009, vol. 363, pp. 19-26.

(Continued)

*Primary Examiner* — Sharon Pregler
(74) *Attorney, Agent, or Firm* — Cantor Colburn LLP

(57) ABSTRACT

The present invention relates to a process for producing cumene and/or sec-butylbenzene comprising contacting benzene with a mixed olefins stream comprising ethylene and an alkylation agent in the presence of a selective alkylation catalyst under selective alkylation conditions.

16 Claims, 2 Drawing Sheets

(56) References Cited

OTHER PUBLICATIONS

Nielsen, "Gasoline Benzene Removal", Process Economics Program, Report No. 273, 2009, table 6.10, p. 6-29, 4 pages.
Slagtern et al., "Cracking of cyclohexane by high Si HZSM-5", Applied Catalysis A: General 375, 2010, pp. 213-221.
Urata et al., "Location of coke on H-ZSM-5 zeolite formed in the cracking of n-hexane", Applied Catalysis A: General 475, 2014, pp. 335-340.
Wei et al., "Production of light olefins and aromatic hydrocarbons through catalytic cracking of naptha at lowered temperature", Studies in Surface Science and Catalysis, vol. 158, 2005, pp. 1223-1230.
Written Opinion for International Application No. PCT/EP2016/070648, International Filing Date Sep. 1, 2016. dated Apr. 11, 2016, 5 pages.
Zimmermann, "Ethylene", Ullmann's Encyclopedia of Industrial Chemistry, 2012, 66 pages.
Zimmermann, "Propene", Ullmann's Encyclopedia of Industrial Chemistry, 2013, 18 pages.

\* cited by examiner

PROCESS FOR PRODUCING CUMENE AND/OR SEC-BUTYLBENZENE USING A MIXED OLEFINS STREAM AS ALKYLATION AGENT

CROSS REFERENCE TO RELATED APPLICATIONS

This application is a National Stage application of PCT/EP2016/070648, filed Sep. 1, 2016, which claims the benefit of European Application No. 15184105.3, filed Sep. 7, 2015, both of which are incorporated by reference in their entirety herein.

The present invention relates to a process for producing cumene and/or sec-butylbenzene comprising contacting benzene with a mixed olefins stream comprising ethylene and an alkylation agent in the presence of a selective alkylation catalyst under selective alkylation conditions.

The commercial production of the benzene derivatives cumene or sec-butylbenzene comprises the alkylation of benzene using propylene or butylene as alkylation agent; see e.g. Hwang and Chen (2010) Cumene Kirk-Othmer Encyclopedia of Chemical Technology 1-10. Conventional processes for producing cumene or sec-butylbenzene are characterized in that no ethylene is fed to the reactor as this would lead to the unwanted side reaction of the ethylene with benzene producing ethylbenzene. However, many processes that produce lower olefins, such as propylene and isobutylene, also produce ethylene. It is therefore required to separate the ethylene from the propylene and/or butylene before said propylene and/or butylene can be used as alkylation agent in a conventional process for producing cumene and/or sec-butylbenzene. Such a separation of ethylene is expensive and energy intensive.

It was an object of the present invention to provide an improved process for selectively producing cumene and/or sec-butylbenzene that does not require separation of the ethylene from the propylene and/or butylene.

The solution to the above problem is achieved by providing the embodiments as described herein below and as characterized in the claims. Accordingly, the present invention provides a process for producing cumene and/or sec-butylbenzene comprising contacting benzene with a mixed olefins stream comprising ethylene and an alkylation agent in the presence of a selective alkylation catalyst under selective alkylation conditions, wherein the alkylation agent is propylene and/or butylene and wherein said selective alkylation catalyst comprises a zeolite of the 12-ring structure type having a 3D cage structure and the selective alkylation conditions comprise a weight hourly space velocity of at least 10 $h^{-1}$, a pressure of 1000-5000 kPa and a temperature of 100-250° C.

In the context of the present invention, it was surprisingly found that by specifically selecting an alkylation catalyst comprising a zeolite of the 12-ring structure type having a 3D cage structure and alkylation conditions comprising a weight hourly space velocity of at least 10 $h^{-1}$, a pressure of 1000-5000 kPa and a temperature of 100-250° C., the alkylation reaction has a very high selectivity towards cumene and/or sec-butylbenzene and a very low selectivity towards ethylbenzene. This allows that specifically cumene and/or sec-butylbenzene is produced even if a mixed olefins stream comprising ethylene used as a feed to the process to provide the alkylation agent.

In the process of the present invention, the ethylbenzene yield preferably is less than 0.2%.

The term "aromatic hydrocarbons" or "aromatics" is very well known in the art. Accordingly, the term "aromatic hydrocarbon" relates to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the 1H NMR spectrum, for example the presence of chemical shifts in the range of from 7.2 to 7.3 ppm for benzene ring protons.

As used herein, the term "C# hydrocarbons", or "C#", wherein "#" is a positive integer, is meant to describe all hydrocarbons having # carbon atoms. Moreover, the term "C#+ hydrocarbons" is meant to describe all hydrocarbon molecules having # or more carbon atoms. Accordingly, the term "C9+ hydrocarbons" is meant to describe a mixture of hydrocarbons having 9 or more carbon atoms. The term "C9+ alkanes" accordingly relates to alkanes having 9 or more carbon atoms.

Accordingly, the process of the present invention involves contacting benzene with a mixed olefins stream comprising ethylene and an alkylation agent in the presence of a selective alkylation catalyst under selective alkylation conditions.

The selective alkylation process of the present invention requires the selection of a "selective alkylation catalyst". Such a selective alkylation catalyst comprises a zeolite of the 12-ring structure type having a 3D cage structure. These specific aluminosilicate zeolites are well known to the skilled man. An overview of their characteristics is for example provided by the chapter on Molecular Sieves in Kirk-Othmer Encyclopedia of Chemical Technology, Volume 16, 811-853; in Atlas of Zeolite Framework Types, 5th edition, (Elsevier, 2001). Accordingly, zeolites of the 12-ring structure type, like for example beta zeolite or zeolite Y, are also characterized in that they have a 3D cage structure. Zeolites having a 3D cage structure are very well known in the art; see Atlas of Zeolite Framework Types; loc.cit. Accordingly, the term "zeolite having 3D cage structure" relates to a zeolite having pores oriented in all 3 directions of the three-dimensional space. A zeolite having pores oriented in only 1 direction of the three-dimensional space is a zeolite having 1D cage structure. A zeolite having pores oriented in 2 direction of the three-dimensional space is a zeolite having 2D cage structure. Preferably, the zeolite used in the process of the present invention further has a pore size of 6.4-8.5 Å. Preferably, the zeolite used in the process of the present invention is selected from the group consisting of beta zeolite and zeolite Y. Depending on the silica-to-alumina ratio of their framework, synthetic faujasite zeolites are divided into zeolite X and zeolite Y. In X zeolites that ratio is between 2 and 3, while in Y zeolites it is 3 or higher. Accordingly, zeolite Y is a synthetic faujasite zeolite having a silica-to-alumina molar ratio ($SiO_2/Al_2O_3$ molar ratio) in their framework of 3 or more. Preferably, the zeolite in the selective alkylation catalyst is in the so-called hydrogen form, meaning that its sodium or potassium content is very low, preferably below 0.1, 0.05, 0.02 or 0.01 wt-%; more preferably presence of sodium is below detection limits. Preferably, the $SiO_2/Al_2O_3$ molar ratio of the zeolite comprised in the selective alkylation catalyst is 1-100, more preferably is 1-50, and most preferably is 1-40.

The selective alkylation process of the present invention requires the selection of "selective alkylation conditions". Such selective alkylation conditions comprise a weight hourly space velocity of at least 10 $h^{-1}$, a pressure of 1000-5000 kPa and a temperature of 100-250° C. Preferably, the selective alkylation conditions comprise a weight hourly space velocity of 10-80 h$^{-1}$, a pressure of 200-3500 kPa and a temperature of 120-250° C. More preferably, the selective alkylation conditions comprise a weight hourly space velocity of 10-80 h$^{-1}$, a pressure of 2200-3200 kPa and a temperature of 160-220° C. Most preferably, the selective alkylation conditions comprise a weight hourly space velocity of 10-50 h$^{-1}$, a pressure of 2500-3000 kPa and a temperature of 180-200° C. The process conditions furthermore preferably comprise an ethylene partial pressure of 400-700 kPa. The process conditions furthermore preferably comprise a propylene partial pressure of 100-200 kPa.

The mixed olefins stream comprising ethylene and an alkylation agent as used in the process of the present invention may be produced by any process for producing mixed olefins. Preferably, the mixed olefins stream is produced by a process selected from the group consisting of catalytic cracking, steam cracking, and syngas-to-olefins process. Such processes are very well described in the prior art; see e.g. Zimmermann, H. and Walzl, R. 2009. Ethylene. Ullmann's Encyclopedia of Industrial Chemistry and Zimmermann, H. 2013. Propene. Ullmann's Encyclopedia of Industrial Chemistry.

Preferably, the process of the present invention further comprises separating the cumene and/or sec-butylbenzene and subjecting the cumene and/or sec-butylbenzene to and subsequent cleavage to produce phenol and ketone. Such a process step for separating the cumene and/or sec-butylbenzene preferably comprises a gas-liquid separation to separate a gaseous stream comprising C1-C4 hydrocarbons and hydrogen from the cumene and/or sec-butylbenzene.

The cumene and sec-butylbenzene oxidation and subsequent cleavage preferably comprises an oxidation step comprising contacting the cumene and/or sec-butylbenzene with an oxidation catalyst and air under oxidation conditions to produce sec-butylbenzen hydroperoxide and/or cumene hydroperoxide and a cleavage step comprising contacting the sec-butylbenzen hydroperoxide and/or cumene hydroperoxide with a cleavage catalyst under cleavage conditions to produce phenol and/or ketone. The oxidation catalyst preferably comprises a transition metal, preferably selected from the group consisting of Mn, Co, Fe, Ni or Cu. The oxidation conditions preferably comprise a temperature of 50-150° C., and a pressure of atmospheric to 1000 kPa. The cleavage catalyst preferably is a homogeneous or heterogeneous acid catalyst. The cleavage conditions preferably comprise a temperature of 40-120° C., a pressure of atmospheric to 1000 kPa gauge and a LHSV between 1-50 h$^{-1}$.

The process step for separating the cumene and/or sec-butylbenzene preferably comprises a distillation step to separate the C6+ hydrocarbons and wherein the thus obtained C6+ hydrocarbons are subjected to distillation to separate the cumene and/or sec-butylbenzene. The distillation to separate the C6+ hydrocarbons preferably further provides a C6 stream, wherein the thus obtained C6 stream is recycled to the alkylation. The distillation of C6+ hydrocarbons preferably further provides a stream comprising heavies, wherein the thus obtained heavies are recycled to the catalytic cracking.

Preferably, the gaseous stream obtained by the gas-liquid separation is contacted with benzene in the presence of an ethylene alkylation catalyst under ethylene alkylation conditions, wherein the alkylation agent is ethylene and wherein the ethylene alkylation catalyst comprises beta zeolite, zeolite Y, ZSM-12, MCM-22 and mordenite and the ethylene alkylation conditions comprise a temperature of 120-250° C. preferably of 200-240° C. a pressure of 1000-5000 kPa gauge, preferably of 2000-3000 kPa gauge, a Weight Hourly Space Velocity (WHSV) of 0.5-20 h$^{-1}$, preferably of 1-10 h$^{-1}$ and a benzene/ethylene molar ratio of 2-10, preferably of 3-6.

The product produced by ethylene alkylation preferably is subjected to gas-liquid separation to separate a gaseous stream comprising C1-C4 alkanes and hydrogen.

The liquid stream provided by the gas-liquid separation of the product produced by ethylene alkylation is preferably subjected to distillation to provide ethylbenzene.

It is noted that the invention relates to all possible combinations of features described herein, particularly features recited in the claims.

It is further noted that the term "comprising" does not exclude the presence of other elements. However, it is also to be understood that a description on a product comprising certain components also discloses a product consisting of these components. Similarly, it is also to be understood that a description on a process comprising certain steps also discloses a process consisting of these steps.

The present invention will now be more fully described by the following non-limiting Examples.

EXAMPLE 1

Selective Alkylation

Figure 1:
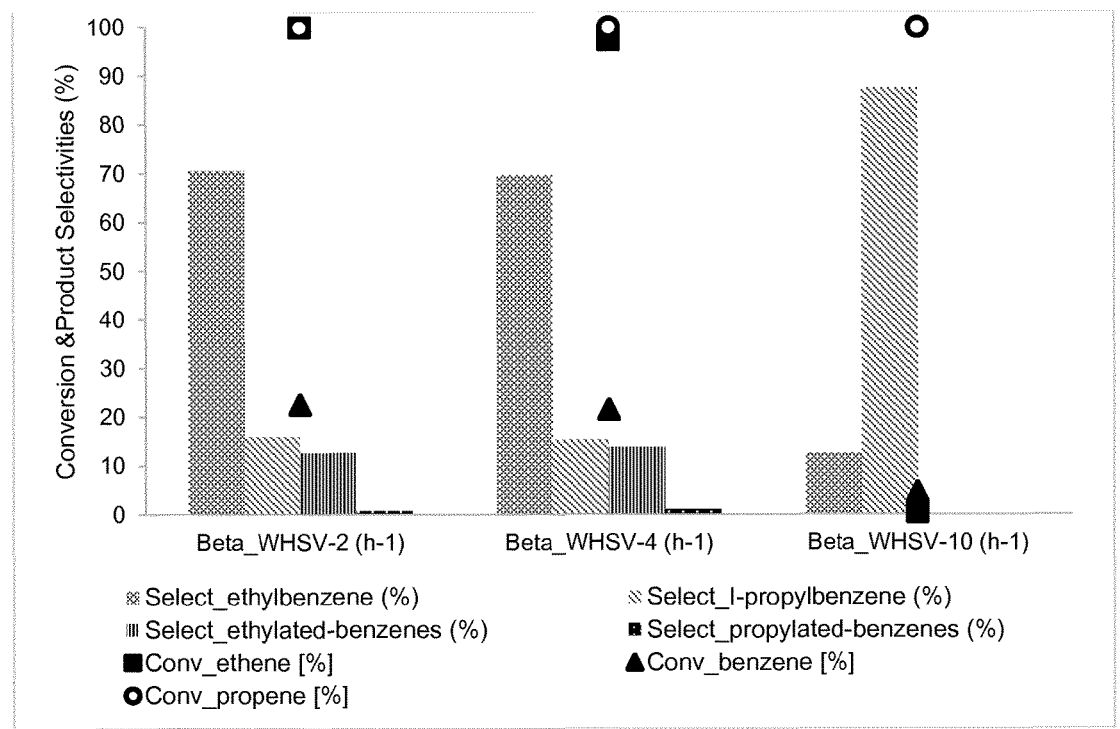
FIG. 1 shows the conversion and product selectivities of the selective alkylation process of the present invention using a beta zeolite-based catalyst.

Mixed olefin feed was obtained by mixing 30 wt % ethylene and 10 wt % propylene with 60 wt % of nitrogen. Similarly, synthetic C6 heart cut composition was obtained by mixing 50 wt % Benzene with other C6 paraffins such as iso-hexane (34 wt %), n-hexane (13 wt) and cyclo-hexane (3 wt %).

Alkylation catalysts were obtained as follows. Beta zeolite with Si/Al ratio of 19 and surface area of 710 m$^2$/g in NH$_4$ form was first calcined in air at 100° C. for three hours then heated to 300° C. for three hours with ramp rates of 3° C./min to remove ammonia and to obtain beta zeolite in the hydrogen form. Further, Y zeolite based catalyst having a Si/Al ratio of 2.6 and a surface area of and 660 m$^2$/g in the hydrogen form was used. Both beta zeolite and Y zeolite were sized by pressing in a die to 69 MPa (10,000 psi) then breaking up the wafer and sieving the catalyst particles to obtain the desired particle size of 125-160 μm.

Alkylation of synthetic C6 heart cut with mixed olefin feed having the above-indicated composition was carried out in high throughput micro catalytic reactor with an internal diameter of 3.5 mm with isothermal heating zone length of 14 cm. In this study, nine parallel micro catalytic reactors were used, wherein the first four reactor were filled with the above-described beta zeolite catalyst with different mass of catalyst to maintain the WHSV of 2, 4, 10 and 2 h$^{-1}$. A second set of four parallel reactors were filled with the above described Y zeolite catalyst with different mass of catalyst to also maintain a WHSV of 2, 4, 10 & 2 h$^{-1}$. The ninth reactor was filled with inert quartz particles to check any reactivity in absence of catalyst activity.

Figure 2:
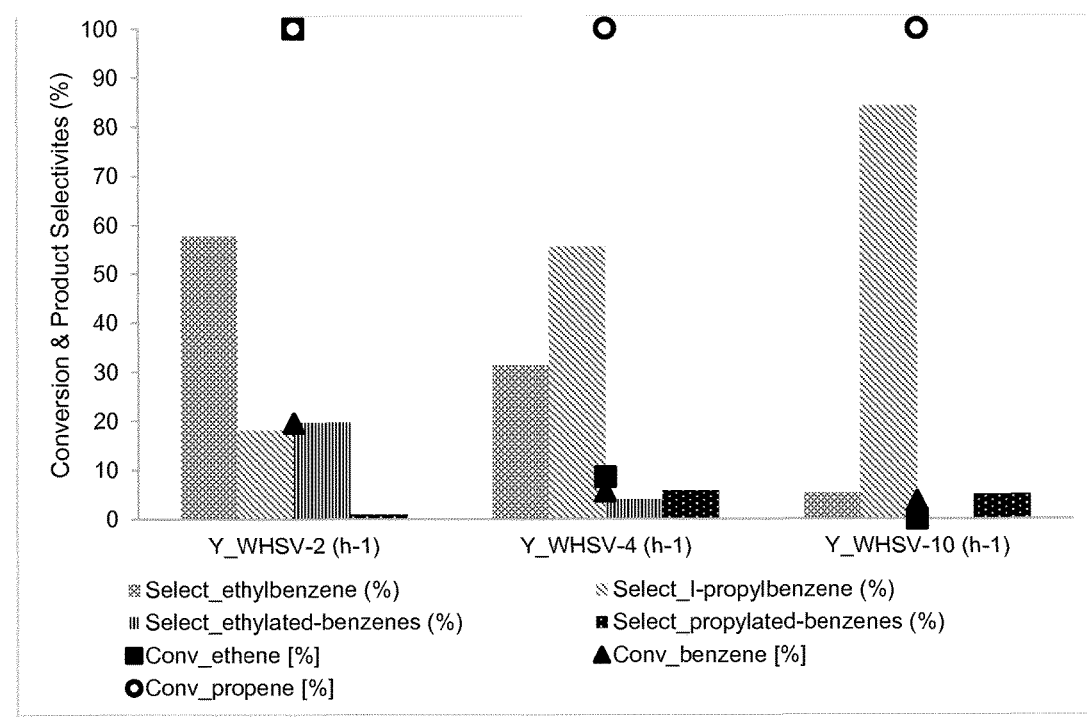
FIG. 2 shows the conversion and product selectivities of the selective alkylation process of the present invention using a zeolite Y-based catalyst.

FIGS. 1 and 2 show the result of the alkylation experiments at the temperature of 200° C., partial pressure of ethylene & propylene 570 and 130 kPa, respectively and benzene/olefins ratio of 4 with varying WHSV from 2 to 10 h$^{-1}$. From these experiments, it is very clear that conversion of propylene is 100% irrespective of catalyst and other parameters. Similarly, complete conversion of ethylene is noticed with both Y Zeolite with WHSV of 2 h$^{-1}$ and Beta zeolite with WHSV 2 & 4 h$^{-1}$. In all cases product selectivity towards ethylbenzene was ≥75% and cumene ≥90% and the main by-products were di-ethylbenzenes and di-isopropyl-benzenes. Surprisingly, Y zeolite catalyst at a space velocity of WHSV 10 h$^{-1}$ or more shows very negligible in ethylene conversion of (~0.2%), particularly when compared with beta zeolite catalyst.

The above experiment clearly demonstrate that WHSV is playing major role for selective alkylation of benzene with propylene in presence of ethylene. In addition, selective alkylation is also affected by nature of catalyst. Compared to beta zeolite catalyst, Y zeolite catalyst at 180 to 200° C., a partial pressure of ethylene & propylene 570 and 130 kPa, respectively, and a benzene/olefins ratio of 4, is showing best result for selectively alkylate benzene with propylene at WHSV of 10 h$^{-1}$.

The other C6 component (iso-hexane, n-hexane and cyclo-hexane) present in the diluted benzene feed conversion was also calculated in the same experimental conditions for the beta zeolite catalyst and the Y zeolite catalyst. Here, it was found that co-feed conversion of the n-hexane, cyclohexane and isohexanes is very limited (<1%) at T=180-200° C. for beta zeolite catalyst and Y zeolite catalyst. In the case of Y zeolite catalyst with WHSV 2 h$^{-1}$ shows little higher conversion of ±5% for iso-hexane at 200° C.

In the context of the present invention, the equations used to calculate conversion, selectivity and WHSV were calculated as describe in the following Table 1

TABLE 1

$$\text{Conversion of benzene} = \frac{\text{Benzene}_{(in)} - \text{Benzene}_{(out)}}{\text{Benzene}_{(in)}}$$

$$\text{Conversion of Ethylene} = \frac{\text{Ethylene}_{(in)} - \text{Ethylene}_{(out)}}{\text{Ethylene}_{(in)}}$$

$$\text{Conversion of Propylene} = \frac{\text{Propylene}_{(in)} - \text{Propylene}_{(out)}}{\text{Propylene}_{(in)}}$$

$$\text{Selectivity of Ethyl benzene}(Y_i) = \frac{\text{Ethylbenzene}(Y_i)}{\text{Total aromatics}}$$

$$\text{Weight Hour Space Velocity (WHSV)} = \frac{\text{Benzene}_{(in)} - \text{Benzene}_{(out)}}{\text{Catalysts weight}}$$

EXAMPLE 2

Comparative

Alkylation experiment was also performed with the above-mentioned feed and conditions with zeolite ZSM-5 having Si/Al ratio of 80 & 280 and Mordenite. It is observed that the conversion of benzene and olefins (ethylene and propylene) is not appreciable compared to Beta and Y zeolite and not suitable for selective alkylation.

The alkylation catalysts as used in Examples 1 and 2 are further described in the following Table 2

TABLE 2

|  | Beta | Mordenite | Zeolite Y | ZSM-5 | ZSM-5 |
|---|---|---|---|---|---|
| Si/Al (mol ratio) | 38 | 13 | 5.2 | 80 | 280 |
| Area (m$^2$/g) | 710 | 425 | 660 | 425 | 425 |
| Cage Structure | 3D | 1D | 3D | 3D | 3D |
| Pore Size (Å) | 7.6 × 6.4 | 6.5 × 7.0 | 7.4 | 5.4 × 5.6 | 5.4 × 5.6 |
| Ring structure type | 12 | 12 | 12 | 10 | 10 |

The invention claimed is:

1. A process for producing cumene and/or sec-butylbenzene, the process comprising
    contacting benzene with a mixed olefins stream comprising ethylene and an alkylation agent in the presence of a selective alkylation catalyst under selective alkylation conditions,
    wherein the alkylation agent is propylene and/or butylene,
    wherein said selective alkylation catalyst comprises a zeolite having a 12-membered ring structure and a 3D cage structure,
    wherein the selective alkylation conditions comprise a weight hourly space velocity of at least 10 h$^{-1}$, a pressure of 1000-5000 kPa and a temperature of 100-250° C.,
    wherein there is a stoichiometric excess of benzene relative to olefins, and
    wherein the ethylbenzene yield of the process is less than 0.2%.

2. The process according to claim 1, wherein the zeolite further has a pore size of 6.4-8.5 Å.

3. The process according to claim 1, wherein the mixed olefins stream is produced by a process selected from the group consisting of catalytic cracking, steam cracking, and syngas-to-olefins process.

4. The process according to claim 1, further comprising separating the cumene and/or sec-butylbenzene and subjecting the cumene and/or sec-butylbenzene to oxidation and subsequent cleavage to produce phenol and ketone.

5. The process according claim 4, wherein said separating the cumene and/or sec-butylbenzene comprises a gas-liquid separation to separate a gaseous stream comprising C1-C4 hydrocarbons and hydrogen from the cumene and/or sec-butylbenzene.

6. The process according to claim 4, wherein said separating the cumene and/or sec-butylbenzene comprises a distillation step to separate the C6+ hydrocarbons and wherein the thus obtained C6+ hydrocarbons are subjected to distillation to separate the cumene and/or sec-butylbenzene.

7. The process according to claim 6, wherein the distillation to separate the C6+ hydrocarbons further provides a C6 stream, wherein the thus obtained C6 stream is recycled to the alkylation.

8. The process according to claim 6, wherein the distillation of C6+ hydrocarbons further provides a stream comprising heavies, wherein the thus obtained heavies are recycled to the catalytic cracking.

9. The process according to claim 5,
    wherein the gaseous stream obtained by the gas-liquid separation is contacted with benzene in the presence of an ethylene alkylation catalyst under ethylene alkylation conditions, wherein the alkylation agent is ethylene and
wherein the ethylene alkylation catalyst comprises beta zeolite, zeolite Y, ZSM-12, MCM-22 and mordenite and
the ethylene alkylation conditions comprise a temperature of 120-250° C., a pressure of 1000-5000 kPa gauge, a Weight Hourly Space Velocity (WHSV) of 0.5-20 h$^{-1}$, and a benzene/ethylene molar ratio of 2-10.

10. The process according to claim 9, wherein the product produced by ethylene alkylation is subjected to gas-liquid separation to separate a gaseous stream comprising C1-C4 alkanes and hydrogen.

11. The process according to claim 10, wherein the liquid stream provided by the gas-liquid separation of the product produced by ethylene alkylation is subjected to distillation to provide ethylbenzene.

12. The process according to claim 4, wherein the cumene and sec-butylbenzene oxidation and subsequent cleavage comprises
an oxidation step comprising contacting the cumene and/or sec-butylbenzene with an oxidation catalyst and air under oxidation conditions to produce sec-butylbenzene hydroperoxide and/or cumene hydroperoxide and
a cleavage step comprising contacting the sec-butylbenzene hydroperoxide and/or cumene hydroperoxide with a cleavage catalyst under cleavage conditions to produce phenol and/or ketone,
wherein said oxidation catalyst comprises a transition metal and the oxidation conditions comprise a temperature of 50-150° C., and a pressure of atmospheric to 1000 kPa and
wherein said cleavage catalyst is a homogeneous or heterogeneous acid catalyst and the cleavage conditions comprise a temperature of 40-120° C., a pressure of atmospheric to 1000 kPa gauge and a LHSV between 1-50 h$^{-1}$.

13. The process according to claim 9, wherein the ethylene alkylation conditions comprise a temperature of 200-240° C., a pressure of 2000-3000 kPa gauge, a Weight Hourly Space Velocity (WHSV) of 1-10 h$^{-1}$ and a benzene/ethylene molar ratio of 3-6.

14. The process according to claim 1, wherein the zeolite is a Y zeolite.

15. The process according to claim 1, wherein a partial pressure of ethylene is 400-700 kPa.

16. The process according to claim 15, further comprising a propylene partial pressure of 100-200 kPa.

* * * * *